United States Patent
Duffy et al.

(10) Patent No.: US 10,889,542 B2
(45) Date of Patent: Jan. 12, 2021

(54) PROCESS FOR PREPARING ELECTRON DEFICIENT OLEFINS

(71) Applicant: Henkel IP & Holding GmbH, Duesseldorf (DE)

(72) Inventors: Cormac Duffy, Dundalk (IE); Marisa Phelan, Roscrea (IE); Barry Burns, Dublin (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 16/438,517

(22) Filed: Jun. 12, 2019

(65) Prior Publication Data

US 2019/0292139 A1    Sep. 26, 2019

Related U.S. Application Data

(63) Continuation of application No. PCT/EP2017/082358, filed on Dec. 12, 2017.

(30) Foreign Application Priority Data

Dec. 23, 2016 (GB) .................................. 1622087.3

(51) Int. Cl.
   *C07C 253/30* (2006.01)
   *C07C 255/23* (2006.01)
   *C07C 255/19* (2006.01)
   *B01J 31/02* (2006.01)

(52) U.S. Cl.
   CPC ......... *C07C 253/30* (2013.01); *B01J 31/0227* (2013.01); *C07C 255/19* (2013.01); *C07C 255/23* (2013.01); *B01J 2231/341* (2013.01); *B01J 2531/38* (2013.01)

(58) Field of Classification Search
   CPC ... C07C 253/30; C07C 255/19; C07C 255/23; B01J 23/20; B01J 27/12; B01J 2531/38; B01J 31/0227; B01J 2231/341
   See application file for complete search history.

(56) References Cited

U.S. PATENT DOCUMENTS

| | | | |
|---|---|---|---|
| 2,756,251 | A | 7/1956 | Joyner et al. |
| 2,763,677 | A | 9/1956 | Jeremias |
| 3,142,698 | A | 7/1964 | Halpern et al. |
| 3,654,340 | A | 4/1972 | Banitt |
| 3,728,375 | A | 4/1973 | Coover, Jr. et al. |

(Continued)

FOREIGN PATENT DOCUMENTS

| | | |
|---|---|---|
| CN | 103922964 A | 7/2014 |
| DE | 2738285 A1 | 3/1979 |

(Continued)

OTHER PUBLICATIONS

Ilangovan, A.; Muralidharan, S. and Maruthamuthu, S. "A Systematic Study on Knoevenagel Reaction and Nazarov Cyclization of Less Reactive Carbonyl Compounds Using Rare Earth Triflates and Its Applications." Journal of the Korean Chemical Society, vol. 55, No. 6, 2011.

(Continued)

*Primary Examiner* — Valerie Rodriguez-Garcia
(74) *Attorney, Agent, or Firm* — Steven C. Bauman

(57) ABSTRACT

This invention relates to a process for preparing electron deficient olefins, such as 2-cyanoacrylates, using an acid catalyzed two-step process including a transesterification reaction followed by a Knoevenagel condensation reaction.

8 Claims, 1 Drawing Sheet

(56) References Cited

U.S. PATENT DOCUMENTS

| | | |
|---|---|---|
| 3,903,055 A | 9/1975 | Buck |
| 3,975,422 A | 8/1976 | Buck |
| 4,003,942 A | 1/1977 | Buck |
| 4,012,402 A | 3/1977 | Buck |
| 4,013,703 A | 3/1977 | Buck |
| 4,202,920 A | 5/1980 | Renner et al. |
| 4,364,876 A | 12/1982 | Kimura et al. |
| 4,512,357 A | 4/1985 | Earl |
| 4,587,059 A | 5/1986 | Harth et al. |
| 5,386,047 A | 1/1995 | Nakos et al. |
| 2,721,858 A | 10/1995 | Joyner et al. |
| 5,455,369 A | 10/1995 | Meier et al. |
| 5,624,699 A | 4/1997 | Lang |
| 5,703,267 A | 12/1997 | Takahashi et al. |
| 6,096,848 A | 8/2000 | Gololobov et al. |
| 6,245,933 B1 | 6/2001 | Malofsky et al. |
| 6,436,866 B1 | 8/2002 | Nishikido et al. |
| 7,569,719 B1 | 8/2009 | McArdle et al. |
| 7,659,423 B1 | 2/2010 | McArdle |
| 7,718,821 B1 | 5/2010 | Bigi et al. |
| 8,022,251 B2 | 9/2011 | McArdle et al. |
| 8,053,589 B1 | 11/2011 | McArdle et al. |
| 8,329,936 B2 | 12/2012 | Friese et al. |
| 8,481,755 B2 | 7/2013 | McArdle et al. |
| 8,686,105 B2 | 4/2014 | McArdle et al. |
| 2012/0023021 A1 | 1/2012 | Seifert et al. |

FOREIGN PATENT DOCUMENTS

| | | |
|---|---|---|
| EP | 0459617 A1 | 12/1991 |
| JP | 2012106982 A | 6/2012 |
| WO | 2015004566 A2 | 1/2015 |
| WO | 2015150882 A1 | 10/2015 |

OTHER PUBLICATIONS

Wen-Bun, Y. et al. "Ytterbium Perfluorooctanesulfonate-Catalyzed Knoevenagel Condensation in Fluorous Biphasic System", Organic Preparations and Procedures International, vol. 39, No. 1, 2007, pp. 71-75.

Narsaiah, A. et al. "An Efficient Knoevenagel Condensation Catalyzed by LaCl3. H2O in Heterogenous Medium." Synthetic communications, vol. 33, No. 21, 2003, pp. 3825-3832.

Remme, N. et al. "Scandium Triflate Catalyzed Transesterification of Carboxylic Esters", Synlett, vol. 20007, No. 3, 2007, pp. 491-493.

Fu, X. et al. "Transesterification catalyzed by samarium tri-2-propoxide", Chinese Journal of Chemistry, vol. 15, No. 1, 1997, pp. 90-93.

Vijayalakshmi, V. et al. "Alkyl and substituted alkyl 2-cyanoacrylates. Part 1. Synthesis and properities" J. Adhesion Sci. Technol., vol. 4, No. 9, 1990, pp. 733-750.

Guseva, T. I. et al. "Organic Chemistry: Synthesis of functionally substituted cyanoacetates" Russian Chemical Bulletin, vol. 42, No. 3, Mar. 1993, pp. 478-480.

Guseva, T. I. et al. "Organic Chemistry: Synthesis of functionally substituted 2-cyanoacrylates" Russian Chemical Bulletin, vol. 43, No. 4, Apr. 1994, pp. 595-598.

Barrett, A. G. and Braddock, D. C. "Scandium (III) or lanthanide (III) triflates as recyclable catalysts for the direct acetylation of alcohols with acetic acid." Chemical Communications, No. 4, 1997, pp. 351-352.

Gololobov, Y. G. et al. "2-Cyanoacrylates. Synthesis, properties and applications" Russian Chemical Reviews, 66 (11), 1997, pp. 953-962.

Senchenya, N. G. et al. "Silicon-containing esters of α-cyanoacrylic acid: synthesis and properties" Russian Chemical Bulletin, vol. 42, No. 5 May 1993, pp. 909-911.

Renner, A. et al. "Cure of Epoxy Resins with Esters of Cyanoacetic Acid" Journal of Polymer Science: Polymer Chemistry Edition, vol. 23, 1985, pp. 2341-2359.

Buck, Carl J. "Unequivocal Synthesis of Bis(2-Cyannoacrylate) Monomers, I. Via Anthracene Adducts" Journal of Polymer Science, Polymer Chemistry Edition, vol. 16, 1978, pp. 2475-2507.

Leelavathi, P. and Ramesh Kumar, S. "Niobium (V) chloride catalyzed Knoevenagel condensation: An efficient protocol for the preparation of electrophilic alkenes" Journal of Molecular Catalysis A: Chemical 240 (2005) pp. 99-102.

Ogiwara, Y. et al. "Indium(III)-Catalyzed Knoevenagel Condensation of Aldehydes and Activated Methylenes Using Acetic Anhydride as a Promoter" J. Org. Chem., 2015, 80, pp. 3101-3110.

Dawar, P. et al."One-Pot Esterification and Amide Formation via Acid-Catalyzed Dehydration and Ritter Reactions", Synthetic Communications, 2014, 44, pp. 836-846.

Opanasenko, M. "Catalytic behavior of metal-organic frameworks and zeolites: Rationalization and comparative analysis" Catalysis Today, 243, 2015, pp. 2-9.

Bartoli, G. et al. "Highly Efficient Solvent-Free Condensation of Carboxylic Acids with Alcohols Catalysed by Zinc Perchlorate Hexahydrate, Zn(ClO4)2•6H2O" Adv. Synth. Catal., 2005, 347, pp. 33-38.

Almasi, M. et al. "Ce(III) and Lu(III) metal-organic frameworks with Lewis acid metalsites: Preparation, sorption properties and catalytic activity inKnoevenagel condensation" Catalysis Today 243, 2015, pp. 184-194.

Viswanadham, B. et al. "The Role of Copper Exchanged Phosphomolybdic Acid Catalyst for Knoevenagel Condensation" Catal. Lett. vol. 146, 2016, pp. 1470-1477.

Cativiela, C. et al. "Synthesis and Preparative Resolution of the trans-Cyclohexane Analogues of Phenylalanine" Eur. J. Org. Chem, 2004, pp. 3898-3908.

Dharma Rao, G. B. and Kaushik, M. P. "Efficient trans-acetoacylation mediated by ytterbium(III) triflate as a catalyst under solvent-free condition." Tetrahedron Letters 52 (2011) pp. 5104-5106.

Lakshmi Kantam, M. et al. "Transesterification of ß-keto esters catalyzed by transition metal complexes in a novel heterogeneous way." Catalysis Letters 62 (1999) pp. 67-69.

Magens, S. et al. "A Nucleophilic Fe Catalyst for Transesterifications under Neutral Conditions." Organic Letters, 2008, vol. 10, No. 1, pp. 53-56.

De Sairre, M.I. et al. "Niobium(V) oxide: a new and efficient catalyst for the transesterification of ß-keto esters." Tetrahedron Letters 46 (2005) pp. 2705-2708.

Seebach, Dieter. "Diisopropyl (2S,3S)-2,3-O-Isopropylidenetartrate", Organic Syntheses., vol. 65, Jan. 1987, p. 230, XP055445562, ISSN: 0078-6209, DOI: 10.15227/orgsyn.065.0230.

Shantha, K. L. et al. "Developments and applications of cyanoacrylate adhesives." J. Adhesion Sci. Technol. vol. 3, No. 4, 1989, pp. 237-260.

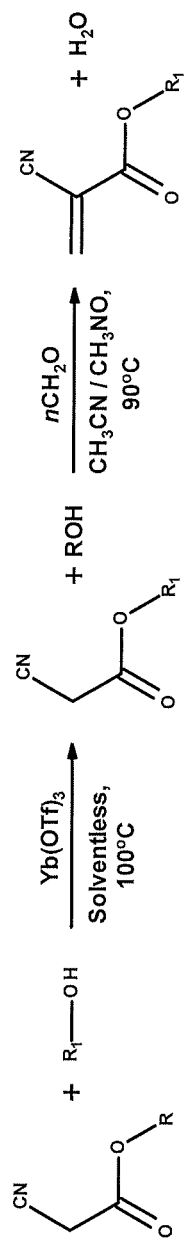

PROCESS FOR PREPARING ELECTRON DEFICIENT OLEFINS

BACKGROUND

Field

This invention relates to a process for preparing electron deficient olefins, such as 2-cyanoacrylates, using an acid catalyzed two-step process including a transesterification reaction followed by a Knoevenagel condensation reaction.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate under base catalysed conditions. During the reaction, cyanoacrylate monomer forms and, due to the basic reaction conditions, polymerises in situ to a prepolymer. The prepolymer is subsequently thermally cracked or depolymerised, yielding cyanoacrylate monomer. This approach has remained essentially the same over time, though improvements and variants have been introduced. See e.g. U.S. Pat. Nos. 6,245,933, 5,624,699, 4,364,876, 2,721,858, 2,763,677 and 2,756,251.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a polyethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russian Chem. Bull.*, 42, 3, 478 (1993) describes functionalized cyanoacetates, many of which were used in the subsequent synthesis of corresponding cyanoacrylates. [See also Guseva et al., *Russian Chem. Bull.*, 43, 4, 595 (1994), and Golobolov and Gruber, *Russian Chem. Rev.*, 66, 11, 953 (1997).]

One of the functionalized cyanoacetates noted in the preceding paragraph is glycidyl cyanoacetate. While the synthesis and characterisation of glycidyl cyanoacetate has been reported, the synthesis, characterisation and provision of performance characteristics of the corresponding glycidyl cyanoacrylate monomer have not to date been published. One explanation for this is that glycidyl cyanoacetate would not survive the conditions of a Knoevenagel reaction to make a cyanoacrylate monomer (initial base catalysis then subsequent exposure to high temperature in presence of strong acids) since epoxides are ring opened under such conditions. And while alternative routes to the glycidyl cyanoacrylate monomer may be conceivable, they would not employ glycidyl cyanoacetate at the outset.

Certain novel compounds having activated methylene groups, including cyanoacetate hybrid molecules, are described and claimed in U.S. Pat. No. 8,481,755.

Other cyanoacetates have been described, such as those with siliconised functionalities. See e.g. Senchenya et al., *Russian Chem. Bull.*, 42, 5, 909 (1993) and European Patent Document No. EP 0 459 617.

The preparation of mono-, di-, tri- and tetra-functional cyanoacetates, albeit as curatives for epoxy resins for adhesive applications, has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

And of course methods for the manufacture of cyanoacrylates are legion.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703]. A variety of other processes for producing cyanoacrylate monomers are known, and some of which are described below.

U.S. Pat. No. 5,703,267 defines a process for producing a 2-cyanoacrylic acid which comprises subjecting a 2-cyanoacrylate and an organic acid to a transesterification reaction.

U.S. Pat. No. 3,654,340 (Banitt) describes and claims an added step in the condensation of formaldehyde and esters of 2-cyanoacetic acid to produce 2-cyanoacrylate esters which consists essentially of catalyzing the reaction by means of a mixture of an acid and the salt of a primary or secondary amine with the same or stronger acid. The acid/amine combination is reported to reduce the extent of polymerization; however, polymerization still occurs and a thermal cracking step is required. The catalytic mixture should have a pH value of 5 or less when exact amounts of its components are dissolved in 25 ml. of water. The '340 patent describes the process to be effective with fluorinated 2-cyanoacrylate esters.

U.S. Pat. No. 3,728,375 is directed to and claims monomeric α-cyanoacrylate esters having esters of an alkyl group of 1-16 carbon atoms, a cyclohexyl group, a phenyl group, an alkoxyalkyl group of 2-16 carbon atoms, a haloalkyl group of 1-10 carbon atoms, an alkenyl group of 2-16 carbon atoms, an arylalkyl group of 7-16 carbon atoms, or an acetoethyl group, and methods of forming the monomeric α-cyanoacrylate esters. Compositions made with these monomeric α-cyanoacrylate esters are prepared containing less than 200 ppm of water.

Recently, a series of U.S. patents have been granted that describe and claim the use of ionic liquids and/or iminium salts in an alternative synthesis of electron deficient olefins. See e.g. U.S. Pat. Nos. 7,659,423; 7,718,821; 7,569,719; 8,022,251; 8,053,589; and 8,686,105.

In addition, International Patent Publication No. WO2015/150882 A1 describes a process for preparing 1,1-disubstituted ethylene monomers using a catalytic amount of an ammonium or iminium salt in homogeneous phase or supported on a solid substrate. The process is reported to be a direct synthesis of such monomers, which does not require a cracking or thermal depolymerization step.

Nonetheless, commercial production of cyanoacrylate monomers ordinarily relies on the depolymerisation of a prepolymer formed under base-catalyzed Knoevenagel condensation reaction conditions, as noted above. Still today the Knoevenagel condensation reaction is believed to remain the most efficient and prevalent commercial method for producing high yields of monofunctional cyanoacrylates.

It would be desirable to not have to resort to thermally induced depolymerisation of a prepolymer produced by the Knoevenagel condensation reaction. This prospect may also enable facile access to highly useful difunctional monomers, such as so-called biscyanaocrylates or hybrid materials of cyanoacrylate and other polymerizable or reactive functionality.

The types of ester side chains that can be introduced to the cyanoacrylic acid ester both in terms of functionality and size is ordinarily limited when a basic catalyst is used in the synthetic steps, largely due to the thermal cracking step that follows in an attempt to liberate a cyanoacrylate monomer. Therefore a synthetic route which avoids the use of a basic catalyst and thermal cracking step is desirable and from a process perspective would be more cost-effective.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

It would be desirable to not have to resort to thermally induced depolymerisation of a prepolymer produced by the Knoevenagel condensation reaction, for many of the reasons stated above. This prospect may also enable facile access to highly useful difunctional monomers, such as so-called biscyanaocrylates or hybrid materials of cyanoacrylate and other polymerizable or reactive functionality. The technical literature is replete with references to acid-catalyzed Knoevenagel condensation reactions, some of which even using lanthanide series elements, such as ytterbium. For instance, reference may be made to *J. Molec. Cat. A: Chemical*, 240, 99-102 (2005); *J. Org. Chem.*, 80, 3101-10 (2015); and *J. Kor. Chem. Soc.*, Vol. 55, No. 6, 1000-1006 (2011).

And U.S. Pat. No. 8,329,936 (Friese) is directed to and claims a method for producing at least one cyanoacrylic acid ester, comprising the following steps: a) transesterification of at least one 2-cyanoacrylic acid ester of a certain formula, with at least one alcohol of a certain formula, in the presence of at least one transition metal catalyst that is formed by reacting at least one hydroxyl group-containing support material with at least one transition metal alkoxide, and b) isolation of the cyanoacrylic acid ester obtained in step a).

Absent from the published literature is a one-pot method to produce electron deficient olefins in situ from a two-step process using an acid catalyst in a transesterification reaction to produce a new electron deficient olefin precursor, which together with aldehyde using an acid catalyst reacts in a Knoevenagel condensation to produce an electron deficient olefin. Until now.

SUMMARY

By employing an acid catalyst in the transesterification reaction and one in the Knoevenagel condensation reaction that follows, electron deficient olefins may be realized in a one-pot, two-step synthetic process. And not having to employ a thermal depolymerization step to yield the electron deficient olefin opens the possibility of facile access to highly useful difunctional monomers, such as so-called biscyanaocrylates or hybrid materials of cyanoacrylate and other polymerizable or reactive functionality.

The process for the preparation of a reactive electron deficient olefin is provided herein, where in one, more focused, aspect, the invention includes the steps of:

(a) reacting an ester of cyanoacetic acid and an alcohol, in the presence of a catalyst comprising a lanthanide element or a transition element (such as a transition metal halide), under appropriate conditions and for a time sufficient to yield a cyanoacetate different from the ester of cyanoacetic acid;

(b) optionally, separating the so-formed cyanoacetate substantially free from the ester of the cyanoacetic acid, the alcohol, and/or the catalyst, and any by-products;

(c) reacting the so-formed cyanoacetate and an aldehyde (or source of an aldehyde), in the presence of a catalyst comprising a lanthanide element or a transition element (such as a transition metal halide), under appropriate conditions and for a time sufficient to yield a cyanoacrylate; and (d) optionally, separating the so-formed cyanoacrylate substantially free from the cyanoacetate, the aldehyde, and/or the catalyst, and any by-products.

In another, more broad, aspect, the invention provides a process for the preparation of a reactive electron deficient olefin precursor that includes the steps of:

(a) reacting a 2-electron withdrawing group-substituted carboxylic acid ester embraced by:

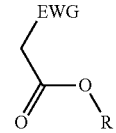

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms; and an alcohol, in the presence of a catalyst comprising a lanthanide element or a transition element (such as a transition metal halide), under appropriate conditions and for a time sufficient to yield an electron deficient olefin precursor embraced by:

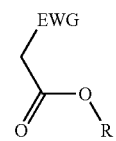

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, provided it is different from R in the 2-electron withdrawing group-substituted carboxylic acid ester;

(b) optionally, separating the so-formed electron deficient olefin precursor substantially free from the ester of the 2-electron withdrawing group-substituted carboxylic acid, the alcohol and/or the catalyst, and any by-products;

(c) reacting the electron deficient olefin precursor and an aldehyde (or a source of aldehyde) in the presence of a catalyst comprising a lanthanide element or a transition element (such as a transition metal halide), under appropriate conditions and for a time sufficient to yield an electron deficient olefin; and (d) optionally, separating the so-formed electron deficient olefin substantially free from the electron deficient olefin precursor, the aldehyde (or source of aldehyde) and/or the catalyst, and any by-products.

BRIEF DESCRIPTION OF THE FIGURE

FIG. 1 depicts a synthetic scheme according to the present invention. More specifically, FIG. 1 shows the transesterification reaction of an ester of cyanoacetic acid with an alcohol at ambient temperature in the presence of ytterbium trifluoromethane sulfonate [Yb(OTf)$_3$] to form a cyanoacetate different from the ester of cyanoacetic acid, followed by the condensation reaction with formaldehyde in the presence of ytterbium trifluoromethane sulfonate [Yb(OTf)$_3$] to generate the target 2-cyanoacrylate.

DETAILED DESCRIPTION

As noted above, the present invention provides a process for the preparation of a reactive electron deficient olefin precursor. In one, more focused, aspect, the invention includes the steps of:

(a) reacting an ester of cyanoacetic acid and an alcohol, in the presence of a catalyst comprising a lanthanide element or a transition element (such as a transition metal halide), under appropriate conditions and for a time sufficient to yield a cyanoacetate different from the ester of cyanoacetic acid;

(b) optionally, separating the so-formed cyanoacetate substantially free from the ester of cyanoacetic acid, the alcohol, and/or the catalyst, and any by-products;

(c) reacting the so-formed cyanoacetate and an aldehyde (or source of an aldehyde), in the presence of a catalyst comprising a lanthanide element or a transition element, under appropriate conditions and for a time sufficient to yield a cyanoacrylate; and (d) optionally, separating the so-formed cyanoacrylate substantially free from the cyanoacetate, the aldehyde, and/or the catalyst, and any by-products.

In another, more broad, aspect, the invention provides a process for the preparation of a reactive electron deficient olefin precursor that includes the steps of:

(a) reacting a 2-electron withdrawing group-substituted carboxylic acid ester embraced by:

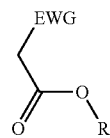

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms; and an alcohol, in the presence of a catalyst comprising a lanthanide element or a transition element, under appropriate conditions and for a time sufficient to yield an electron deficient olefin precursor embraced by:

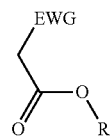

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, provided it is different from R in the 2-electron withdrawing group-substituted carboxylic acid ester;

(b) optionally, separating the so-formed electron deficient olefin precursor substantially free from the 2-electron withdrawing group-substituted carboxylic acid ester, the alcohol and/or the catalyst, and any by-products;

(c) reacting the electron deficient olefin precursor and an aldehyde (or a source of aldehyde), in the presence of a catalyst comprising a lanthanide element or a transition element, under appropriate conditions and for a time sufficient to yield an electron deficient olefin; and (d) optionally, separating the so-formed electron deficient olefin substantially free from the electron deficient olefin precursor, the aldehyde (or source of aldehyde) and/or the catalyst, and any by-products.

Reference to FIG. 1 may be useful to appreciate further the present invention, which is described in more detail below and in the Examples section that follows.

As an initial reactant in the inventive processes is the so-described ester of the 2-electron withdrawing group-substituted carboxylic acid. Representative examples of the ester of the 2-electron withdrawing group-substituted carboxylic acid used as a reactant include esters of malonic acid, glycolic acid, alkyl (e.g., ethyl) nitroacetic acid, alkyl (e.g., ethyl) haloacetic (like bromoacetic, chloroacetic, and iodoacetic), and cyanoacetic acid (i.e., cyanoacetate), some of which are commercially available for instance from Aldrich Chemical Co. A particularly desirable example of 2-electron withdrawing group-substituted carboxylic acid is cyanoacetic acid.

The amount of the ester of the 2-electron withdrawing group-substituted carboxylic acid that should be used in the inventive process is in the range of about 0.5 to about 2 equivalents, such as about 0.8 equivalents.

Together with the ester of the 2-electron withdrawing group-substituted carboxylic acid as an initial reactant in the inventive processes is an alcohol.

The alcohol may be any mono-, di- or multi-functional hydroxyl compound. Mono-, di- or multi-functional $C_{1-20}$ alkanols, $C_{2-20}$ alkenols, and $C_{2-20}$ alkynols, whether straight chain, branched, cyclic or fused, may be used. Aromatic alcohols, such as phenol, benzyl alcohol and derivatives thereof, may be used.

The alcohol should be used in an amount of about 0.5 to about 2 equivalents, such as about 0.8 equivalents.

The alcohol and the compound should be used in a molar ratio of about 0.5 to about 2 equivalents, such as about 0.8 equivalents.

As noted, the catalyst is one that comprises lanthanide element or a transition element. The catalyst is acidic in nature, as measured or determined by its ability to donate a hydrogen (proton or hydrogen ion, $H^+$), or, alternatively, its ability to form a covalent bond with an electron pair.

To the lanthanide element or the transition element is bonded, coordinated or complexed, as appropriate, one or more ligands. The ligands may be selected for instance from conventional leaving groups used in organic synthetic schemes. Halogens, tosylates, mesylates, nitrates, and triflates are chief among ligands that are suitable for use herein.

A prime example of a lanthanide element suitable for use in this connection is ytterbium, though others may also be useful, such as lanthanum, cerium, samarium, europium, and dysprosium. Prime examples of a transition element suitable for use in this connection is niobium, zirconium or scandium, with niobium being particularly desirable in this regard.

Desirable catalysts for use in the inventive process include ytterbium trifluoromethane sulfonate [Yb(OTf)$_3$] and niobium halides, such as niobium chloride.

The catalyst should be used in an amount of up to about 20 mol %, such as about 10 mol %.

The electron deficient olefin precursor so formed by the inventive processes may be a variety of olefins having an electron withdrawing group attached to a carbon atom that is alpha to the carbonyl of a carboxylic acid.

This electron deficient olefin precursor contains a methylene linkage having at least one electron withdrawing substituent attached thereto, where the electron withdrawing substituent is selected from cyano or nitrile, alkoxy or aryloxy, carboxyl (such as carboxylic acids and carboxylic esters), sulphonic acids, carbonyls, halogens (e.g., F, Cl, Br, and I), nitro, isocyanate, sulfoxide and phosphine oxide.

Representative examples of these electron deficient olefin precursors include, malonic acid esters, ethyl nitroacetate, cyanoacetic acid esters (i.e., cyanoacetate), and glycolic acid esters, some of which are commercially available for instance from Aldrich Chemical Co. A particularly desirable example is cyanoacetate.

In a desirable embodiment, the reactive electron deficient olefin precursor so formed will be a 2-cyanoacetate.

Representative examples of 2-cyanoacetates so formed by the inventive processes include those having ester groups of methyl, ethyl, propyl, isoamyl, propargyl, butyl, pentyl, hexyl, octyl, nonyl, oxononyl, decyl, dodecyl, allyl, ethynyl, butenyl, cyclohexyl, phenyl, phenethyl, tetrahydrofurfuryl, chloroethyl, 2,2,2-trifluoroethyl, hexafluoroisopropyl, methoxymethyl, thiomethoxymethyl, methoxyethyl, thiomethoxyethyl, methoxybutyl, thiomethoxybutyl, ethoxyethyl, thioethoxyethyl, propoxyethyl, thioproxyethyl, butoxymethyl, thiobutoxymethyl, butoxyethyl, thiobutoxyethyland dimethyl siloxane esters of 2-cyanoacrylic acid. This recitation is by no means however exhaustive.

While no solvent is ordinarily needed, the reaction of the inventive processes may proceed in solvent either forming a solution or a suspension. Solvents that may be used include acetonitrile, benzonitrile, chlorobenzene, nitromethane, tetrachloroethene, toluene, THF, 1,4-dioxane, and (poly)ethylene glycol dialkyl ethers, and of course combinations thereof. Ionic liquids may also be used as the solvent. The reaction of the inventive processes may proceed with or without heating or cooling, depending of course on the specific reactants and the scale of the reaction.

While the reaction ordinarily occurs at ambient temperature, gentle heating up to a temperature of 70° C. may be applied. The temperature may be reached through an external heating element or internally by means of the exotherm that may be generated depending on the identity of the reactants. The temperature of the reaction should be controlled however to accommodate any such exothermic processes.

The time of reaction may be monitored by reference to the formation of the desired electron deficient olefin precursor product. $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

The so-formed electron deficient olefin precursor is then used in the Knoevenagel condensation reaction of the second step. The other reactant in the second step is an aldehyde (or source of aldehyde). The aldehyde source may be aldehyde compounds having the structure R—CH=O, where R is hydrogen or vinyl. The aldehyde compound may be an aldehyde itself or a source of an aldehyde, such as one that yields an aldehyde like formaldehyde under reaction conditions. The aldehyde compound in a desirable embodiment includes formaldehyde (or a source thereof, such as paraformaldehyde), formalin, 1,3,5-trioxane, methylene diacetate, dimethoxymethane, or vinyl aldehydes, such as acrolein.

The source of aldehyde should be used in an amount of 1.0-2.0 equivalents, such as 2.0 equivalents.

Once again, in the Knoevenegal condensation reaction of the second step, a catalyst is acidic in nature, as measured or determined by its ability to donate a hydrogen (proton or hydrogen ion $H^+$), or, alternatively, its ability to form a covalent bond with an electron pair. To the lanthanide element or the transition element is bonded, coordinated or complexed, as appropriate, one or more ligands. The ligands may be selected for instance from conventional leaving groups used in organic synthetic schemes. Halogens, tosylates, mesylates, nitrates and triflates are chief among ligands that are suitable for use herein.

A prime example of a lanthanide element suitable for use in this connection is ytterbium, though others may also be useful, such as scandium, lanthanum, and samarium. A prime example of a transition element suitable for use in this connection is niobium.

Desirable catalysts for use in the Knoevenagel condensation reaction of the second step of the inventive processes include ytterbium trifluoromethane sulfonate [Yb(OTf)$_3$] and niobium chloride.

Here, the catalyst should be used in an amount of 0-20 mol %, such as 0.5 to 10 mol %, desirably 1 to 5 mol %, based on the electron deficient olefin precursor.

The electron deficient olefin so formed by the inventive processes may be a variety of olefins having at least one electron withdrawing group attached thereto. In a desirable embodiment, the electron deficient olefin so formed will have two or more electron withdrawing groups attached thereto, which may be the same or different. In a desirable embodiment, the electron deficient olefin so formed will have two or more electron withdrawing groups attached thereto, which may be the same or different. For instance, the electron deficient olefin may be a compound having one end terminating with a cyanoacrylate, cyanopentadienoate, cyanohexadienoate, or alkylene derived from dimalonate and another end terminating with a group selected from branched and unbranched alkyl esters, esters containing aromatics and hetrocylic nuclei, (meth)acrylates, cyanoacrylates, siloxanes, blocked and unblocked isocyanates, anhydrides, silanes, vinyls, acetylenes, and epoxies.

Particularly desirable products have two electron withdrawing groups attached thereto which are different, such as 2-cyanoacrylate esters.

Representative examples of 2-cyanoacrylate esters so formed by the inventive processes include those having ester groups of methyl, ethyl, propyl, isoamyl, propargyl, butyl, pentyl, hexyl, octyl, nonyl, oxononyl, decyl, dodecyl, allyl, ethynyl, butenyl, cyclohexyl, phenyl, phenethyl, tetrahydrofurfuryl, chloroethyl, 2,2,2-trifluoroethyl, hexafluoroisopropyl, methoxymethyl, thiomethoxymethyl, methoxyethyl, thiomethoxyethyl, methoxybutyl, thiomethoxybutyl, ethoxyethyl, thioethoxyethyl, propoxyethyl, thioproxyethyl, butoxymethyl, thiobutoxymethyl, butoxyethyl, thiobutoxyethyl and dimethyl siloxane esters of 2-cyanoacrylic acid. This recitation is by no means however exhaustive.

While no solvent is ordinarily needed, the transesterification reaction of the first step of the inventive processes may proceed in solvent either forming a solution or a suspension. Solvents that may be used include acetonitrile, benzonitrile, chlorobenzene, nitromethane, tetrachloroethene, toluene, THF, 1,4-dioxane, and (poly)ethylene glycol dialkyl ethers. Ionic liquids may also be used as the solvent. The Knoevenagel condensation reaction of the second step of the inventive processes ordinarily is performed with solvent, any of those noted above being a suitable choice. The reaction of the inventive processes may proceed with or without heating or cooling, depending of course on the specific reactants and the scale of the reaction.

While the transesterification reaction of the first step ordinarily occurs at ambient temperature, gentle heating up to a temperature of 70° C. may be applied. The temperature may be reached through an external heating element or internally by means of the exotherm that may be generated depending on the identity of the reactants. The temperature of the reaction should be controlled however to accommodate any such exothermic processes. Likewise, the temperature conditions of the Knoevenagel condensation reaction of the second step may be moderated in similar fashion.

The time of reaction of the transesterification reaction of the first step may be monitored by reference to the formation of the desired electron deficient olefin precursor product. $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions. Likewise, the reaction time and monitoring of the progress of the Knoevenagel condensation reaction of the second step may be similar.

The following example is intended to illustrate but in no way limit the present invention.

EXAMPLES

Example 1

To a 50 mL round bottomed flask was added 6.34 g (0.056 mol) of ethyl cyanoacetate, 5.00 g (0.0675 mol) of distilled n-butanol and 3.47 g (6.75 mmol, 10 mol %) of ytterbium triflate. The flask was fitted with a magnetic stirrer and rigorously stirred at 100° C. for 8.5 hours. A crude $^1$H NMR taken at this point indicated a conversion to butyl cyanoacetate of ~60.60%. The flask was then charged with 1.80 g (0.060 mol) of paraformaldehyde, 10 mL of nitromethane and 5 mL of acetonitrile, fitted with a reflux condenser and the reaction temperature was reduced to 90° C. The reaction was stopped after 6.5 hours. The relative conversion of cyanoacetate to cyanoacrylate was monitored by 500 MHz $^1$H NMR, with the observations shown below.

| Relative Conversion by NMR: | 2 hr: | 25.32% |
|---|---|---|
| | 4 hr: | 26.67% |
| | 6.5 hr: | 15.50% |

Example 2

To a 50 ml round bottomed flask is added 7.01 g (0.062 mol) of ethyl cyanoacetate, 4.15 g (0.056 mol) of n-butanol and 10 mL of nitromethane. The flask is fitted with a reflux condenser and magnetic stirrer before being immersed in an oil bath at a temperature of 105° C. The mixture is stirred at this temperature for a period of time of 30 minutes before a mixture of 3.47 g (6.75 mmol, 10 mol %) of ytterbium triflate in 5 ml of acetonitrile is added. After a period of time of about 6 hours 3.00 g (0.10 mol) of paraformaldehyde is added. The reaction is stopped after a period of time of 6 hours, with the relative conversion of cyanoacrylate to cyanoacrylate monitored by 500 MHz $^1$H NMR.

Example 3

To a 50 ml round bottomed flask is added 7.01 g (0.062 mol) of ethyl cyanoacetate, 4.936 g (0.056 mol) of 2-pentanol and 10 mL of nitromethane. The flask is fitted with a reflux condenser and magnetic stirrer before being immersed in an oil bath at a temperature of 105° C. The mixture is stirred at this temperature for a period of time of 30 minutes before a mixture of 3.47 g (6.75 mmol, 10 mol %) of ytterbium triflate in 5 ml of acetonitrile is added. After a period of time of about 6 hours 3.00 g (0.10 mol) of paraformaldehyde is added. The reaction is stopped after a period of time of 6 hours, with the relative conversion of cyanoacrylate to cyanoacrylate monitored by 500 MHz $^1$H NMR.

What is claimed is:

1. A one-pot process for the preparation of a cyanoacrylate, steps of which comprise:

(a) reacting the ester of cyanoacetic acid and an alcohol, in the presence of a catalyst comprising a lanthanide element, wherein the lanthanide element comprises ytterbium, and wherein the alcohol is present in an amount of from 0.5 equivalents to 2 equivalents relative to said ester, under appropriate conditions and for a time sufficient to yield a cyanoacetate different from the ester of cyanoacetic acid;

(b) reacting the so-formed cyanoacetate from step (a) with a source of aldehyde selected from the group consisting of formaldehyde, paraformaldehyde, formalin, 1,3,5-trioxane, methylene diacetate, dimethoxymethane, and acrolein in the presence of a catalyst comprising a lanthanide element, wherein the lanthanide element comprises ytterbium, under appropriate conditions and for a time sufficient to yield a cyanoacrylate; and (c) optionally, separating from the reaction mixture the so-formed cyanoacrylate to be substantially free from the ester of the cyanoacetic acid, the alcohol, the catalyst(s) and/or the cyanoacetate, and by-products.

2. A one-pot process for the preparation of an electron deficient olefin, steps of which comprise:
(a) providing as reactants:
(i) a 2-electron withdrawing group-substituted methylene compound embraced by:

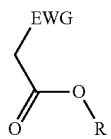

wherein EWG represents an electron withdrawing group selected from the group consisting of cyano, halogens, nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms; and
(ii) an alcohol;
wherein the alcohol is present in an amount of from 0.5 equivalents to 2 equivalents relative to the 2-electron withdrawing group-substituted methylene compound;
(b) reacting the 2-electron withdrawing group-substituted methylene compound and the alcohol in the presence of a catalyst comprising a lanthanide element or a transition element, under appropriate conditions and for a time sufficient to yield an electron deficient olefin precursor embraced by:

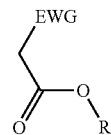

wherein EWG represents an electron withdrawing group selected from the group consisting of cyano, halogens, nitro, isocyanate, sulfoxide and phosphine oxide; and R here represents straight chain, branched, cyclic or fused $C_{1-20}$ alkyl, $C_{2-20}$ alkenyl, $C_{2-20}$ alkynyl, and $C_{6-20}$ aryl or $C_{7-20}$ alkaryl, with or without substitution or interruption by one or more heteroatoms, provided it is different from R in step (a)(i);

(c) reacting the electron deficient olefin precursor and a source of aldehyde selected from the group consisting of formaldehyde, paraformaldehyde, formalin, 1,3,5-trioxane, methylene diacetate, dimethoxymethane, and acrolein in the presence of a catalyst comprising a lanthanide element wherein the lanthanide element comprises ytterbium, under appropriate conditions and for a time sufficient to yield an electron deficient olefin; and (d) optionally, separating from the reaction mixture the so-formed electron deficient olefin to be substantially free from the reactants and by-products.

3. The one-pot process of claim 1, wherein the catalyst comprising a lanthanide element has one or more ligands bound to the element(s).

4. The one-pot process of claim 3, wherein the one or more ligands is selected from halogens, triflates, nitrates, mesylates or tosylates.

5. The one-pot process of claim 1, wherein the alcohol is any mono-, di- or multi-functional hydroxyl compound.

6. The one-pot process of claim 1, wherein the alcohol is any mono-, di- or multi-functional $C_{1-20}$ alkanol, $C_{2-20}$ alkenol, $C_{2-20}$ alkynol.

7. The one-pot process of claim 1, wherein the alcohol is an aromatic alcohol.

8. The one-pot process of claim 1, wherein the alcohol is phenol or benzyl alcohol.

* * * * *

UNITED STATES PATENT AND TRADEMARK OFFICE
CERTIFICATE OF CORRECTION

PATENT NO. : 10,889,542 B2
APPLICATION NO. : 16/438517
DATED : January 12, 2021
INVENTOR(S) : Cormac Duffy, Marisa Phelan and Barry Burns Page 1 of 1

It is certified that error appears in the above-identified patent and that said Letters Patent is hereby corrected as shown below:

In the Specification

Column 1, Line 40 change "polyethylene glycol)" to --poly (ethylene glycol)--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*